(12) United States Patent
Soyemi et al.

(10) Patent No.: US 7,881,892 B2
(45) Date of Patent: Feb. 1, 2011

(54) STANDARDIZATION METHODS FOR CORRECTING SPECTRAL DIFFERENCES ACROSS MULTIPLE SPECTROSCOPIC INSTRUMENTS

(75) Inventors: Olusola O. Soyemi, Shrewsbury, MA (US); Babs R. Soller, Northboro, MA (US)

(73) Assignee: University of Massachusetts, Boston, MA (US)

( * ) Notice: Subject to any disclaimer, the term of this patent is extended or adjusted under 35 U.S.C. 154(b) by 981 days.

(21) Appl. No.: 11/337,912

(22) Filed: Jan. 23, 2006

(65) Prior Publication Data

US 2007/0112258 A1  May 17, 2007

Related U.S. Application Data

(60) Provisional application No. 60/645,070, filed on Jan. 21, 2005.

(51) Int. Cl.
  G06F 19/00 (2006.01)
  G01D 18/00 (2006.01)
  G01J 3/28 (2006.01)
(52) U.S. Cl. .................................. 702/85; 356/326
(58) Field of Classification Search ............. 702/76, 702/77, 85; 356/325, 326, 328
  See application file for complete search history.

(56) References Cited

U.S. PATENT DOCUMENTS 6,002,477 A * 12/1999 Hammer .................. 356/307
6,983,176 B2 * 1/2006 Gardner et al. ............ 600/310
2005/0259254 A1 * 11/2005 Soller et al. ............... 356/328

OTHER PUBLICATIONS

Wang et al., "Multivariate Instrument Standardization," Analytical Chemistry 63: 2750-2758 (1991).
Bouveresse et al., "Standardisation of near-infrared spectrometric instruments: A review," Vibrational Spectroscopy 11: 3-15 (1996).
Bouveresse et al., "Application of standardization methods to correct the spectral differences induced by a fibre optic probe used for the near-infrared analysis of pharmaceutical tablets," Journal of Pharmaceutical and Biomedical Analysis 18: 35-42 (1998).
Soyemi et al., "Standardization Method for Correcting Spectral Differences across Multiple Units of a Portable Near Infrared-Based Medical Monitor," Proceedings of SPIE vol. 5702 (Optical Diagnostics and Sensing V 2903), pp. 135-142 (2005).

* cited by examiner

*Primary Examiner*—Bryan Bui
(74) *Attorney, Agent, or Firm*—Fish & Richardson P.C.

(57) ABSTRACT

The invention relates to systems and methods for measuring properties of samples with standardized spectroscopic systems. The methods can include (i) measuring, with a first spectroscopic system, spectra of at least three different reference targets; (ii) calibrating the first spectroscopic system; (iii) measuring, with the first spectroscopic system, a spectrum of a known reference specimen having a known value of the property; (iv) generating a model for the measured property using the spectrum of the known reference specimen; (v) measuring, with a second spectroscopic system, the spectra of at least three different reference targets; (vi) calibrating the second spectroscopic system; (vii) applying the model to the second spectroscopic system; (viii) measuring a spectrum of the sample using the second spectroscopic system; and (ix) determining a value of the property using the model.

43 Claims, 12 Drawing Sheets

FIGURE 6A
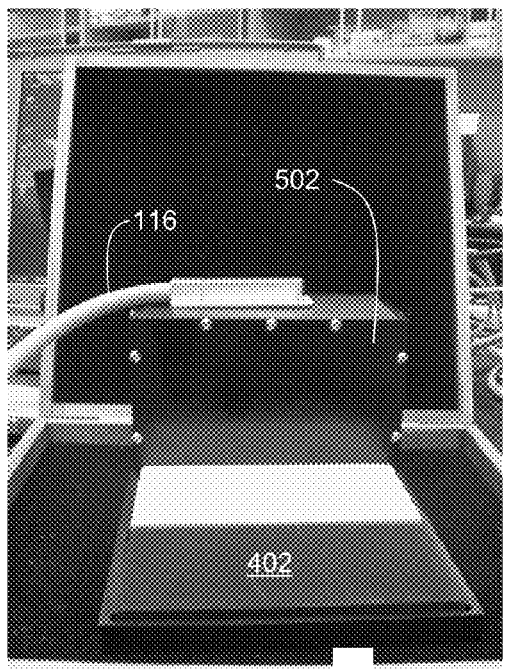
FIGURE 6B
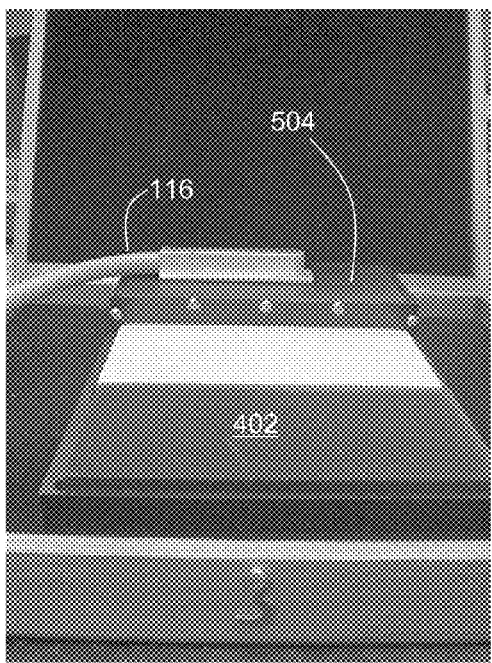
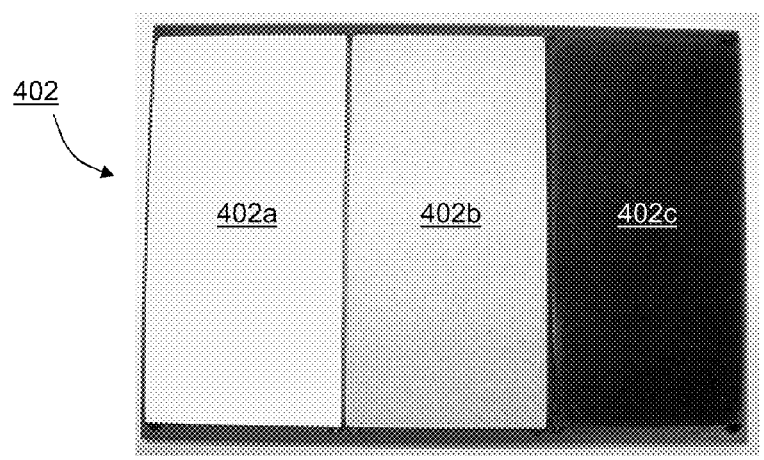
FIGURE 7

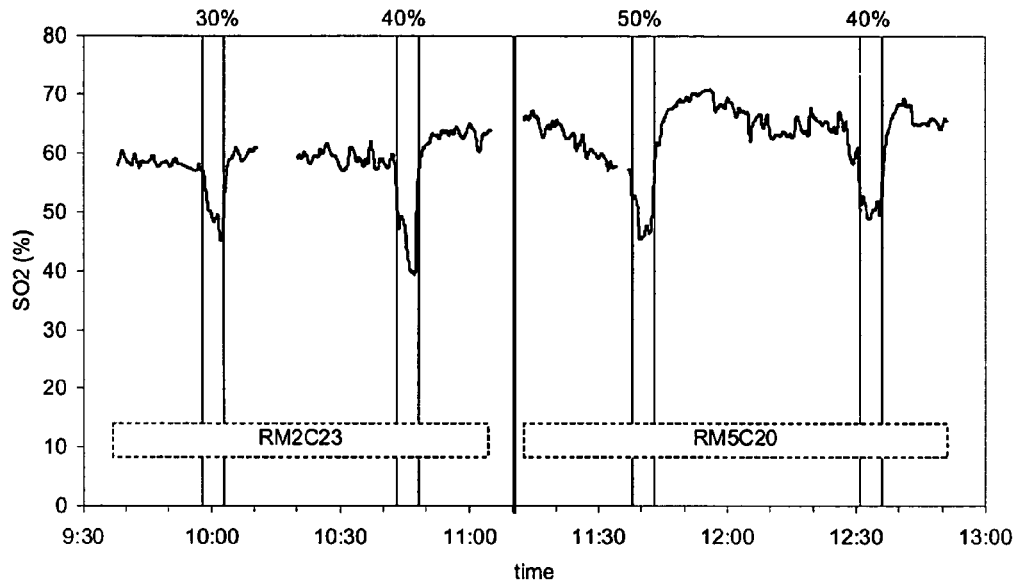
FIGURE 13A          FIGURE 13B
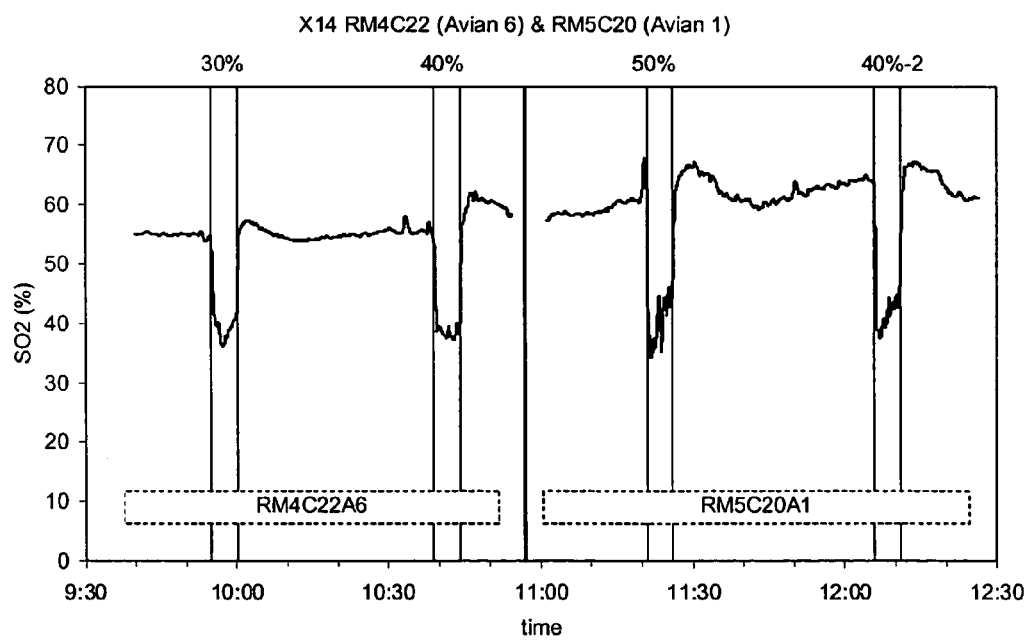
FIGURE 14A          FIGURE 14B

STANDARDIZATION METHODS FOR CORRECTING SPECTRAL DIFFERENCES ACROSS MULTIPLE SPECTROSCOPIC INSTRUMENTS

CROSS-REFERENCE TO RELATED APPLICATIONS

This application claims priority from U.S. Provisional Patent Application No. 60/645,070, filed on Jan. 21, 2005, the contents of which are incorporated herein by reference in their entirety.

STATEMENT AS TO FEDERALLY SPONSORED RESEARCH

Funding for the work described herein was provided by the U.S. Army Medical Research Command, Contract Number DAMD17-03-1-0005. The Federal Government may have certain rights in the invention.

TECHNICAL FIELD

This invention relates to spectrometer systems and methods, and more particularly to spectrometer systems for reflectance measurements.

BACKGROUND

Optical spectroscopy is commonly used to determine the concentration of chemical species in gaseous, liquid, and solid samples. The amount of light absorbed by a particular chemical species in a sample is often linearly related to its concentration through Beer's Law, $A=\epsilon lc$, where A is termed absorbance, $\epsilon$ is a constant specific to the chemical species, l is the path length of light, and c is the concentration of the species. $A=\log(I_0/I)$, where $I_0$ is the intensity of light incident on a sample containing the chemical to be measured, and I is the intensity of light after it has passed through the sample.

For nontransparent materials, including complex materials such as liquids, powders, tablets, natural materials (e.g., soil and agricultural products), blood, skin, and muscle, optical information can be collected via diffuse reflectance spectroscopy. In this setting, $A=\log(I_{100}/I_R)$, where $I_{100}$ is the amount of light reflected from a 100% reflecting diffuse reflectance standard, the equivalent of the incident light, and $I_R$ is the amount of light reflected from the solution under study. The concentration of a chemical component in one of these complex materials is related to A, though often not linearly. Sophisticated mathematical techniques, such as, for example, partial least squares ("PLS") regression and other multivariate calibration methods can be used to determine a relationship between the concentration of a chemical species and absorbance by the sample. Once these calibration models are derived, they can be used to determine the chemical composition of a sample by measuring absorbance of the sample in the transmittance or reflectance mode.

In the laboratory, it is relatively straightforward to measure the absorbance A. One method uses a temperature controlled dual beam spectrograph. The sample solution is placed in one chamber, and the amount of light transmitted through the sample is measured. The solvent alone is placed in the second chamber where the incident light is measured. The ratio is determined electronically and the absorbance reported.

Laboratory spectrographs are generally large, expensive, and not portable. Recently, smaller spectrographs have been introduced that allow absorbance measurements to be performed in the "field," meaning that the spectrometer equipment can be brought to the sample, rather than requiring that the sample be brought to the lab.

Spectroscopic measurements are now commonly made of agricultural products, in the ocean, in forests, on manufacturing production lines, and on the human body. Most of these measurements are made in the reflectance mode in which a fiber optic based sensor directs light to the sample and measures light reflected back from the sample. Field measurements are often made in an ongoing, continuous manner, to observe temporal changes of a quantity measured spectroscopically. Sometimes these measurements are made in a "hostile" environment, where it is difficult to make electrical measurements because electronic instruments experience interference (e.g., in an MRI machine) or degradation (e.g., due to a smoke stack or waste water).

Usually spectroscopic measurements are made by first collecting light from the 100% reflectance standard, storing that number, then attaching the sensor to the sample and collecting a series of spectra. The initial reference measurement of the 100% reflectance standard is used to calibrate absorbance from all subsequent sample spectra. This process, unfortunately, can introduce significant error, especially when the target absorbance changes are small and present in a complex, interfering chemical mixture, such as those studied in the field. Over time there can be changes in the lamp output and the detector sensitivity, which alter the intensity and spectral temperature of light impinging on the sample. If these changes are not detected and corrected in real time in the absorbance calculation, the measured value of A can be erroneous, and an accurate concentration of the measured quantity may not be made.

In addition, because different spectrographs can respond differently to the same sample, spectrographs may need to be standardized so that the different spectrographs provide consistent information. Because the cost of developing clinical parameter models based on partial least squares ("PLS") regression can be prohibitive, the practical application of PLS regression models to quantitative tissue spectroscopy depends largely on the feasibility of applying PLS models developed on a primary ("master") instrument to tissue measurements acquired with other ("slave") instruments. From a measurement standpoint, a non-invasive sensor that utilizes PLS-modeled absorbance spectra to predict clinical parameters of interest is a relatively simple instrument, consisting primarily of a light source, a wavelength dispersive device combined with a detector (spectrometer), and a fiber-optic tissue sampling probe. From a manufacturing standpoint, however, it is difficult to exactly calibrate the performance of these components in individual sensor units. Consequently, the optical spectrum of a single tissue sample that is measured with two different instruments can result in mismatched spectra reported by the two instruments.

If the two measured spectra were applied to a PLS model that was developed on one of the sensors, estimates of the modeled parameter will also be different. Approaches developed to solve this problem typically require the measurement of one or more samples (transfer samples) by both the master and slave instruments, with the purpose of calculating an "instrument correction factor," or "transfer function" that can be used to match the spectral output of the slave device to that of the master device. These standardization approaches, however, require that the transfer samples be selected from the same population used in deriving the calibration model, which is not practical in medical applications where the "samples" are human tissue. While one might consider the use of tissue-mimicking phantom samples as viable transfer samples, batch-to-batch errors in phantom creation as well as the poor long-term stability of virtually all known tissue phantom formulations, can severely limit their use in this regard.

SUMMARY

The invention disclosed herein relates in part to methods and systems for standardizing spectral outputs across multiple spectroscopic sensor instruments or systems in which traceable physical standards are used to match the wavelength and photometric output across the different sensor systems.

As described herein, the spectral output of multiple spectroscopic systems can be standardized or "calibrated" to correct for spectral differences caused by the specific physical peculiarities of each individual system. The new methods use traceable physical standards, e.g., reflectance targets, to match the wavelength and photometric output across different systems and do not require the use of samples similar to the sample to be measured. This approach is applicable to any spectroscopic systems that make repeatable, quantitatively accurate reflectance or absorbance measurements. This is particularly true for applications that use multivariate calibration methods to measure complex samples such as tissue, blood, urine, saliva, chemical and pharmaceutical products, agricultural products, and optical spectra from environmental samples.

In general, in a first aspect, the invention features methods of measuring a property of a sample with a spectroscopic system. The methods include (i) measuring, with a first spectroscopic system, spectra of a first set of at least three different reference targets, each target having a known, unique reflectivity spectrum; (ii) calibrating the first spectroscopic system based on the spectra of the first set of reference targets measured by the first spectroscopic system; (iii) measuring, with the first spectroscopic system, a spectrum of a known reference specimen having a known value of the property; (iv) generating a model for the measured property in the first spectroscopic system using the spectrum of the known reference specimen; (v) measuring, with a second spectroscopic system, spectra of a second set of at least three different reference targets, each target having a known, unique reflectivity spectrum; (vi) calibrating the second spectroscopic system based on the spectra of the second set of reference targets measured by the second spectroscopic system; (vii) applying the model to the second spectroscopic system; (viii) measuring a spectrum of the sample using the second spectroscopic system; and (ix) determining a value of the property using the model.

Embodiments of the new methods can include any of the following features.

Calibrating the first spectroscopic system can include calculating a set of calibration coefficients $a_1$, $b_1$, and $c_1$. Calibrating the second spectroscopic system can include calculating a set of calibration coefficients $a_2$, $b_2$, and $c_2$. The three different unique reflectivity spectra for the first set of targets can be the same as the three different unique reflectivity spectra for the second set of targets. Alternatively, at least one, e.g., two or all three, of the three different unique reflectivity spectra for the first set of targets can be different than one of the three different unique reflectivity spectra for the second set of targets.

The first and second spectroscopic systems can be calibrated using a wavelength standard prior to measuring the spectra of the reference targets. The wavelength standard can be a mercury-argon lamp. The reflectivity spectra of the reference targets can be traceable to a standard. The methods can further include determining an optimum stand-off distance between a probe of the first and second spectroscopic systems and a reference target. In some embodiments, determining an optimum stand-off distance can include measuring a reflectance intensity as a function of a distance between the probe and the reference target, and selecting the distance at which the reflectance intensity is highest.

The spectrum of the sample measured using the second spectroscopic system can be corrected prior to determining a value of the property. The correction can include normalizing the spectrum with a standard normal variate algorithm.

In some embodiments the value of the property can be determined using a modified Beer's law equation. The sample can include human tissue or can be selected from the group consisting of blood, urine, and saliva. The sample can also be selected from the group consisting of tissue, blood, agricultural products, pharmaceuticals, natural products, and petroleum. The sample can be an in vitro sample or an in vivo sample.

In various embodiments, the property can be an amount of hemoglobin in the sample, oxygen saturation, content, or pressure in the sample, a pH of the sample, a concentration of lactate or glucose in the sample, or a concentration of sodium ions, potassium ions, or calcium ions in the sample.

The reflectivities of the set of at least three different reference targets measured with the first and second spectroscopic systems can span a range from about 2% to about 99%, e.g., 10% to about 90%. In various embodiments, the reflectivities of the sets of at least three different reference targets measured with the first and second spectroscopic systems can be about 2%, about 50%, and about 99%, or about 5%, about 45%, and about 95%.

In general, in another aspect, the invention features standardized spectroscopic systems that include a light source, a spectrograph, a probe for receiving light from the light source that is reflected by a target, a processor configured to calculate calibration constants from reflectivity spectra of at least three different reference targets obtained by shining light from the light source on the at least three different reference targets and recording the reflectivity spectra received by the probe and measured by the spectrograph, and a memory for storing the calibration constants.

In certain embodiments, the processor can include computer program code or machine instructions that direct the processor to carry out the calculation of the calibration constants. The probe can be a fiber optic probe, and the system can include at least one stand-off for maintaining the probe at a selected distance from the target. The processor can be further configured to correct spectra obtained with the system using a standard normal variate algorithm or to determine a value of a property of a sample by fitting a measured spectrum of the sample to a modified Beer's law equation.

In some embodiments, the systems can include a translation stage coupled to a driver for transporting the at least three different reference targets past a fixed position of the probe. Alternatively, the system can include a translation stage coupled to a driver for transporting the probe past a fixed position of the at least three different reference targets.

In certain embodiments, the systems include the at least three different reference targets, and the processor can be further configured to provide prompts to an operator performing a series of steps comprising a standardization sequence or to automatically perform a series of steps comprising a standardization sequence without operator intervention. In other embodiments, the processor can be further configured to prompt an operator to re-standardize the spectroscopic system after a selected time interval has elapsed since a previous standardization sequence.

In another aspect, the invention features methods of measuring a property of a sample by (i) calibrating a spectroscopic system, where calibrating the spectroscopic system includes measuring, using the spectroscopic system, spectra of at least three different reference targets, each having a known, unique reflectivity spectrum, and calibrating the spectroscopic system based on the spectra of the at least three different targets, where the spectroscopic system includes a model that correlates a measured spectrum of the sample to a property of the sample; (ii) measuring a spectrum of the sample using the calibrated spectroscopic system; and (iii) determining a value of the property using the model.

Embodiments of these methods can include any of the following features. Calibrating the spectroscopic system can include calculating a set of calibration coefficients a, b, and c. The measured spectrum of the sample can be corrected prior to determining a value of the property, and the at least three different reference targets can have reflectivities of about 2%, about 50%, and about 99%.

In another aspect, the invention features methods of constructing a spectroscopic model for a property of a sample by (i) measuring, using a spectroscopic system, spectra of at least three different reference targets, each having a known, unique reflectivity spectrum; (ii) calibrating the spectroscopic system based on the spectra of the at least three different targets; (iii) measuring, using the spectroscopic system, a spectrum of a known reference specimen having a known value of the property; and (iv) generating a model for the measured property using the spectrum of the known reference specimen.

In certain embodiments, the model can be generated by fitting the spectrum of the known reference specimen to a mathematical equation describing a relationship between the spectrum and the measured property.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more implementations are set forth in the accompanying drawings and the description below. Other features and advantages will be apparent from the description and drawings, and from the claims.

DESCRIPTION OF DRAWINGS

FIG. 6A is a photograph showing a 70 mm stand-off block positioned atop a standardized reflectance target.

FIG. 6B is a photograph showing a 7.5 mm stand-off block positioned atop a standardized reflectance target.

FIG. 7 is a photograph showing a reflectance target having three regions of different standardized reflectance.

FIGS. 13A and 13B are graphs showing percent oxygen saturation for a volunteer subject, measured with two different standardized measurement systems.

FIGS. 14A and 14B are graphs showing percent oxygen saturation for a different volunteer subject, measured with two additional different standardized measurement systems.

Like reference symbols in the various drawings indicate like elements.

DETAILED DESCRIPTION

As described herein, reflectance measurements are made by multiple spectroscopic systems on traceable standards to standardize the different systems, and specific mathematical procedures are used to process spectra obtained by the spectroscopic systems before the spectra are used to calculate properties of complex chemical entities in the measured samples. For example spectra of tissue, blood, grains, and gasoline can be measured by the standardized systems to calculate properties, such as the hemoglobin concentration in blood, sugar concentration in grains, moisture content in grains, and the octane content in gasoline. Using the techniques and systems described herein, measured spectra are transformed to remove instrument-to-instrument variations from the measured spectra so that spectra collected by different instruments appear as if they were generated by the same instrument.

Spectroscopic Systems

Figure 1:
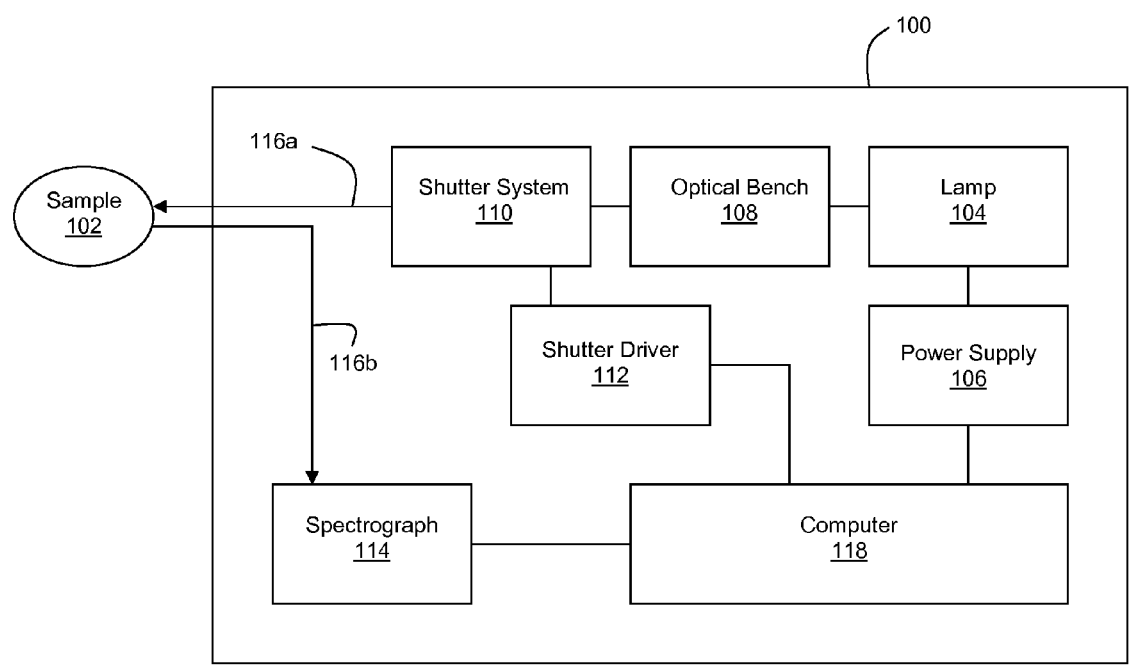
FIG. 1 is a schematic diagram of a spectroscopic system.

As shown in FIG. 1, an exemplary portable fiber-optic-based spectroscopic system 100 for collection of reflectance spectra from a sample 102 located remotely from the system can include a lamp 104, a power supply for the lamp 106, an optical bench 108, a shutter system 110, a driver for the shutter system 112, a spectrograph 114, a fiber optic cable 116, and a computer 118. Light from the lamp is manipulated by optics within the optical bench 108 and controlled by a shutter system 110 that is driven by a shutter driver 112. Light can be passed by the shutter system 110 into a first portion of the fiber optic cable 116a and guided to the sample 102.

When light is guided to the sample in fiber optic cable 116a, light reflected from the sample 102 is guided by a second portion of the fiber optic cable 116b from the sample 102 to the spectrograph 114. Reflected light from the sample 102 is analyzed by the spectrograph 114 to gather information about the sample 102. The analysis is calibrated by spectral analysis of light reflected from targets having a known reflectivity spectrum, $R(\lambda)$, that is traceable to absolute physical standards, as explained in more detail herein.

The system 100 further includes a computer 118 (e.g., an on-board computer or a remote computer connected to system 100) for controlling the shutter driver 112, the spectrograph 114, and for processing, storing, and displaying data from the spectrograph.

The spectrograph 114 can be any portable spectrograph that can be operated by computer control, for example, an Ocean Optics USB2000 spectrograph (available from Ocean Optics Inc., Dunedin, Fla.) with a grating optimized for performance in the wavelength range of 500 nm to 1000 nm. The spectrograph detector can be a 2048 pixel element shallow-well linear CCD-array. The spectrograph can be equipped with a 200 micron wide slit to increase resolution, a collection lens to increase light collection efficiency at the detector, and a long pass filter to block light with a wavelength less than 475 nm from reaching the detector. The USB2000 spectrograph can interface with the computer 118 through either a USB or RS232 port.

The optical bench 108 is used to set up and maintain proper alignment of the lamp 104, the optical fiber 116, the spectrograph 114, and other optical components to enhance the accuracy and reproducibility of the system 100 as a reflectance spectroscopy measurement system. The optical bench 108 can be fabricated from aluminum because aluminum can be easily machined to close tolerances and has high thermal conductivity to promote heat dissipation and minimize thermal stress and distortion on the components of the system 100.

The lamp 104 can be a white light source (e.g., a tungsten bulb such as Welch Allyn 7106-003, available from Welch Allyn, Skaneateles Falls, N.Y.) that is driven by a specially designed power supply 106 to allow for fast ramp-up and stable operation of the lamp. The lamp 104 can be a continuous wave ("cw") light source or a pulsed light source. The lamp 104 is housed within its own machined reflector, so that it is relatively easy to replace when necessary, and its optical alignment is assured through the design of the optical bench. The lamp rests against mechanical stops that ensure that it is accurately located with respect to the fiber optic cable 116a. Light from the lamp 104 is focused down a center axis of the optical bench 108 by a reflector (e.g., an ellipsoidal reflector). Although the light sources described above are thermal light sources (e.g., a tungsten filament lamp), the light source can generally be any broadband light source (e.g., a broadband light emitting diode, a laser).

Figure 2:
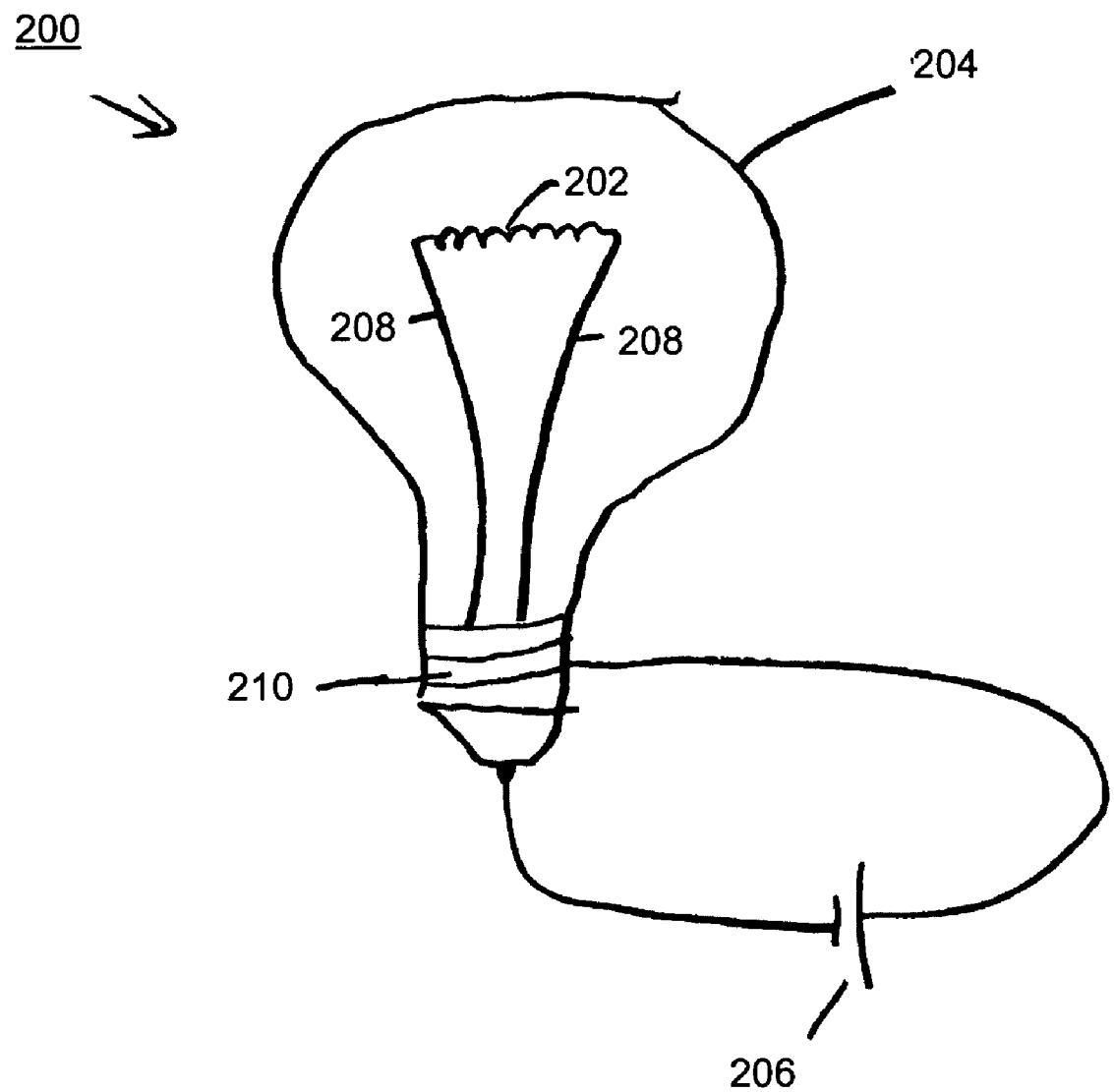
FIG. 2 is a schematic diagram of an incandescent lamp used in the spectroscopic system of FIG. 1.

The general lamp configuration of a thermal light source is illustrated in FIG. 2, which shows an incandescent light source 200 that includes an electrically resistive filament 202 within a transparent bulb 204. The filament 202 is generally made of tungsten. The bulb 204 can be made of glass, quartz, or other materials and can be evacuated or can be filled with a halogen gas, an inert gas, or a mixture of gases. Electrical current is supplied from a power supply 206 to the filament 202 through electrically conductive lead wires 208 that are electrically connected to the base 210 of the light source. The electrical current causes the filament to radiate as a black body. The power supply 206 can supply direct current (DC) or alternating current (AC).

The total electromagnetic energy emitted by a black body, according to Stefan's law, is equal to $$I_T = \sigma e T^4, \tag{1}$$

where $I_T$ is the intensity of the emitted energy, $\sigma$ is the Stefan-Boltzmann constant, e is the emissivity of the black body material, and T is the temperature of the black body in Kelvin. The spectral distribution of the energy emitted from the black body is equal to $$\rho_T(\lambda) = 8\pi hc/\lambda^5 (e^{hc/k\lambda T} - 1), \tag{2}$$

where $\rho_T(\lambda)$ is the intensity as a function of wavelength, $\lambda$ is the wavelength, h is Planck's constant, c is the velocity of light, k is Boltzmann's constant, and T is temperature of the source. Thus, the total light output from a filament lamp is proportional to the fourth power of the temperature, and the spectral distribution is similarly a strong function of the filament temperature.

When power is first applied to a filament lamp 200, the filament 202 heats up until the power emitted by the filament (both radiant power and conducted power) equals the power applied to the filament (i.e., the voltage across the filament multiplied by the current through it). The resistance, R, of the filament is a function of the filament's temperature, T, $$R = f(T). \tag{3}$$

Nearly all incandescent lamp filaments are made of tungsten, which has a positive coefficient of resistance versus temperature. Thus, as the filament heats up, its resistance increases and its power dissipation declines according to the relation $P = V^2/R$, where P is the dissipated power, V is the voltage drop across the filament, and R is the resistance of the filament. If a constant voltage is applied across the lamp, the filament 202 reaches initial equilibrium within seconds and provides nominally stable light output. However, as the filament support wires 208 heat up they conduct less heat away from the filament 202, the filament becomes hotter, and its light output increases. Similarly, as the lamp base 210 and mount heat up, the filament 202 continues to increase in temperature, and its light output rises. Although these effects increase the filament temperature only slightly, the strong dependence of light output on temperature means that small increases in filament temperature translate into relatively large increases in light output. Because of the long time required for a lamp and its support structure to reach thermal equilibrium, an hour can be required to reach stable light output. If the temperature of the environment changes, the lamp's output will also vary with the temperature of the environment.

As electrical power is initially supplied and dissipated in filament 202, the temperature, T, of the filament rises, causing the filament to emit light having an intensity and spectral distribution given by Equations (1) and (2). To achieve a stable light intensity and spectral distribution from the light source 200, the temperature of the filament is stabilized. By measuring the electrical properties of the filament 202, a lamp driver circuit can indirectly measure the filament temperature. Because the resistance of the filament 202 is a direct function of the filament temperature, a constant filament temperature can be maintained by driving the filament at a constant resistance.

The light source 200 can be an incandescent lamp, for example, a Welch-Allyn 7106-0003 lamp, having a desired operating filament resistance of 5 Ohms when supplied with 5 Volts and 1 Amp of current. Other incandescent filament lamps can also be used.

Light from the light source can be used to analyze the electromagnetic reflectance spectrum of a sample. Light can be ported from the light source to the sample in one leg of a fiber optic cable system to illuminate the sample and to excite the sample optically. Light reflected from the sample can be ported from the sample to a spectrograph that measures the reflectance spectrum. Cross talk between light used to excite the sample and reflected light from the sample is reduced by spatially separating the ends of the optical fibers that shine light onto the sample and the ends of optical fibers that receive reflected light from the sample. A third leg of the fiber optic cable system ports light from the light source to the spectrograph, and can be used to calibrate the reflectance spectrum.

Figure 3A:
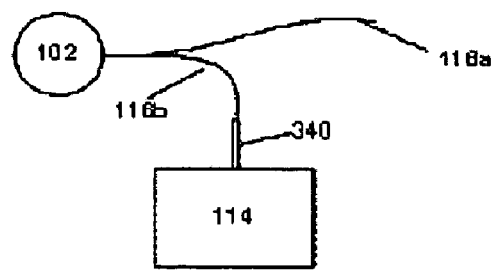
FIG. 3A is schematic diagram of an arrangement of a fiber optic cable used in the spectroscopic system of FIG. 1 for delivering light to a sample and a fiber optic cable for porting reflected light from the sample to a spectrograph.
Figure 3B:
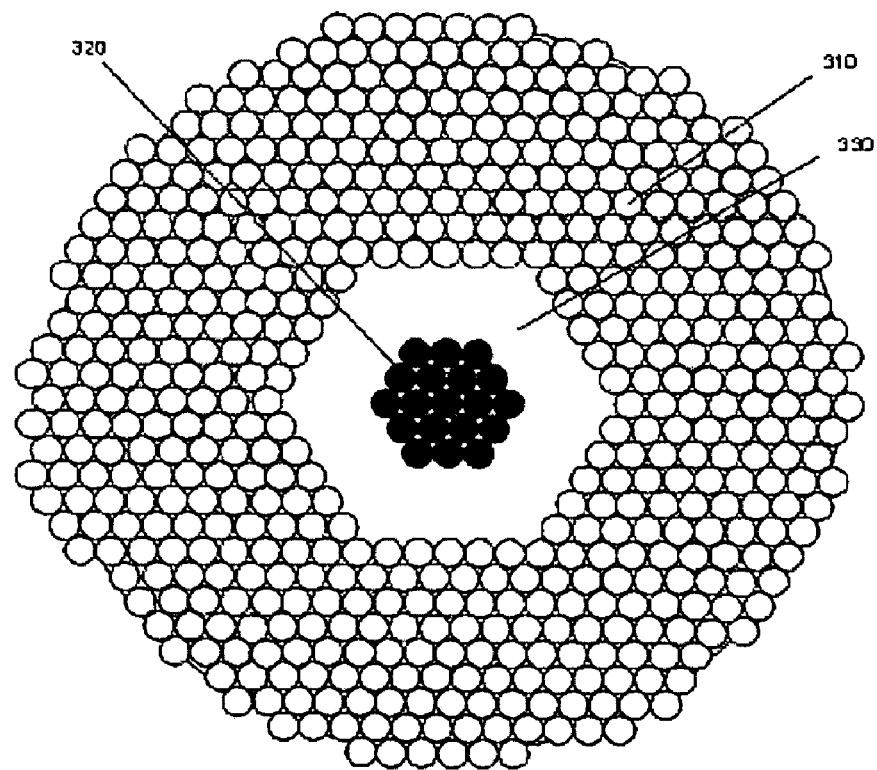
FIG. 3B is a schematic end view of an arrangement of fibers in the fiber optic cable for delivering light to a sample and the fibers in the fiber optic cable for porting reflected light from the sample to a spectrograph.

As shown in FIG. 3A, the fiber optic cable can include two different fiber bundles 116a and 116b. The sample bundle 116a merges with the return bundle 116b at the sample end of the bundles (i.e., at the end of the bundles that is proximal to the sample 102), and the return bundle 116b ports light reflected from the sample 102 to the spectrograph 114. As shown in FIG. 3B, the sample bundle 116a is a ring of individual fibers 310 unconnected to the light source 104 that surrounds a bundle of fibers 116b formed of individual fibers 320 that return reflected light back to the spectrograph 114. In one implementation, the outer ring of individual fibers 310 in the sample cable 116a contains approximately 2666 50 µm glass fibers with a numerical aperture (NA) of 0.66. The central bundle of fibers 320 in the return cable 116b returns reflected light from the sample 102 to the spectrograph 114, and in one implementation can contain 109 50 µm glass fibers with an NA of 0.66. In certain implementations, a gap 330 between the central bundle 320 and outer ring 310 is about 4 mm. Gap 330 can be filled with a solid material (e.g., a metal, such as aluminum, plastic, such as polycarbonate) to position and mechanically fix the central bundle 320 with respect to outer ring 310. At the sample end of the fibers, all fibers are oriented approximately perpendicularly to the surface of sample 102.

To reduce the NA to 0.22, as required for the spectrograph, a 600 mm fused silica rod 340 can be placed at the end of the fiber bundle 116b. To prevent stray light from entering the spectrograph 114, a black, light-absorbing epoxy can be used to surround the silica rod 340.

Standardization or Calibration of Multiple Systems

Standardization measurements, as described in more detail below, are made with a predetermined calibration model for every spectroscopic system so that the spectra measured by different systems are consistent with each other. Standardization of multiple units or systems is necessary because instrument-dependent errors can be introduced into the measured spectra.

Standardization measurements are made on a system, including the entire optical assembly of the system (including, e.g., the light source, the optical bench, the spectrograph, and any fiber optic cable assemblies to deliver light to and from a sample or subject) to calibrate the system, and the same standardization measurement procedure is used for each new system that is manufactured. Additionally, the standardization of an instrument can be updated on a regular basis as the instrument ages, and the light sources degrade, the optical systems become misaligned, the optical fibers break, and/or the detector sensitivity changes.

The pixel elements of the spectrograph 114 can be calibrated with a wavelength standard such as a mercury-argon lamp (e.g., available from Ocean Optics Inc.) by directing the output of the mercury-argon lamp into the sample bundle 116b. The known wavelengths of easily identifiable mercury and argon spectral emission lines are compared to the spectrum measured by the 2048 pixel elements of the spectrograph 114, and the comparison is used to perform a pixel-to-wavelength calibration of the system 100 by linear regression.

Figure 4:
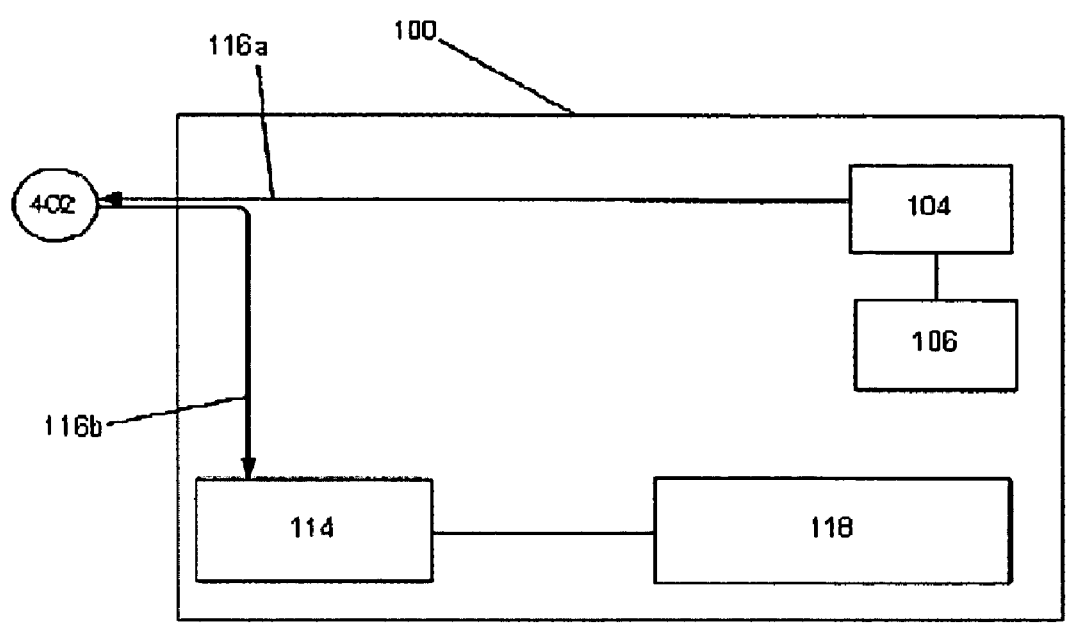
FIG. 4 is a schematic view of a spectroscopic system used to measure the reflectivity spectrum of a physical standard.

The absorbance spectra measured by different systems of the same sample can be standardized as follows. As shown in FIG. 4, the sample bundle 116b of the spectroscopic system 100 can be placed in contact with or at a fixed and repeatable distance from a standard reflectance target 402 having a known reflectivity spectrum over the wavelengths of interest, $R^{std}(\lambda)$. The reflectance target 402 has a reflectivity spectrum that is traceable to absolute standards, for example, standards maintained by the National Institute of Standards (NIST), and can be obtained, for example, from Labsphere Inc. (North Sutton, N.H.). The reflectivity spectrum of the reflectance target 402 can be constant over the wavelengths of interest, but needs to be precisely known only over the wavelengths of interest for which the system will be used.

Positioning of sample bundle 116a relative to reflectance target 402 can be an important consideration when calibrating a measurement system. Measurement of a reflectance value from a particular target may correspond only to the target's nominal reflectance if the light from sample bundle 116a is incident on a surface of the target within a relatively narrow distribution of angles. In general, the incidence angle of the light relative to a surface normal of the sample can take on any value from 0 to 90 degrees, and an angle of incidence that produces an optimum result (i.e., an ideal reflectance measurement, or a maximum in measured light intensity) can be determined by either or both of reflectance target 402 and the components of the measurement system. For example, for certain reflectance targets and measurement systems, incident light from sample bundle 116a may be directed to be incident on a target surface at an angle of about 8 degrees from a surface normal.

Direct contact between sample bundle 116a and a surface of a reflectance target essentially provides for a normal direction of incidence of incoming light. To adjust the measured reflectance to match the nominal reflectance of target 402, therefore, measurement systems include mechanisms for adjusting the angle of incidence of the light. This adjustment can be performed in many cases by varying the distance between bundle 116a and the surface. The measured diffuse reflectance counts (D) depend upon the probe-to-target distance (PTD). For certain measurement systems, the quantity D has a local maximum that depends on the PTD (i.e., the functional form is of an increase in D with increasing or decreasing PTD, a plateau region around the optimum PTD value, and a decline in D thereafter). The PTD value that is typically selected for use in measurement systems—the value that yields the largest D signal—produces an angle of incidence that closely corresponds with the angle required to match the measured and nominal reflectances of target 402.

After the sample bundle 116b is placed in proximity with the reflectance target 402, a spectrum of the reflectance target 402, $R^{meas}(\lambda)$, is recorded by the spectrograph 114 and stored in the computer 118. Spectra, $R_X^{meas}(\lambda)$, are measured with the system 100 for at least three reflectance targets 402 having different traceable reflectivity spectra, $R_X^{std}(\lambda)$, where the index, X, indicates the nominal absolute and measured reflectivity. For example, spectra can be recorded for five reflectance targets 402 having NIST-traceable, wavelength-independent reflectivities of 2%, 10%, 50%, 75%, and 99%, or for three reflectance targets having reflectivities of 2%, 50%, and 99%. Generally, two or more, e.g., at least three, four, five, or more targets are selected which span a range of possible reflectivities to be encountered in spectral measurements of actual samples. For example, if an instrument will be used only in a reflectance range of 40% to 60%, then the reflectivity of the different targets could be: 42%, 46%, 50%, 54%, and 58%; or alternatively, the reflectivities of the targets could be 40%, 50%, and 60%. Other ranges are also possible. For example, the reflectivities of a selected set of targets could be 70%, 80%, and 90%; or, alternatively, 25%, 50%, and 75%. The methods herein are sufficiently flexible to allow for a wide variety of targets having different reflectivities from about 0.1% to about 99.9% to be selected.

Figure 5A:
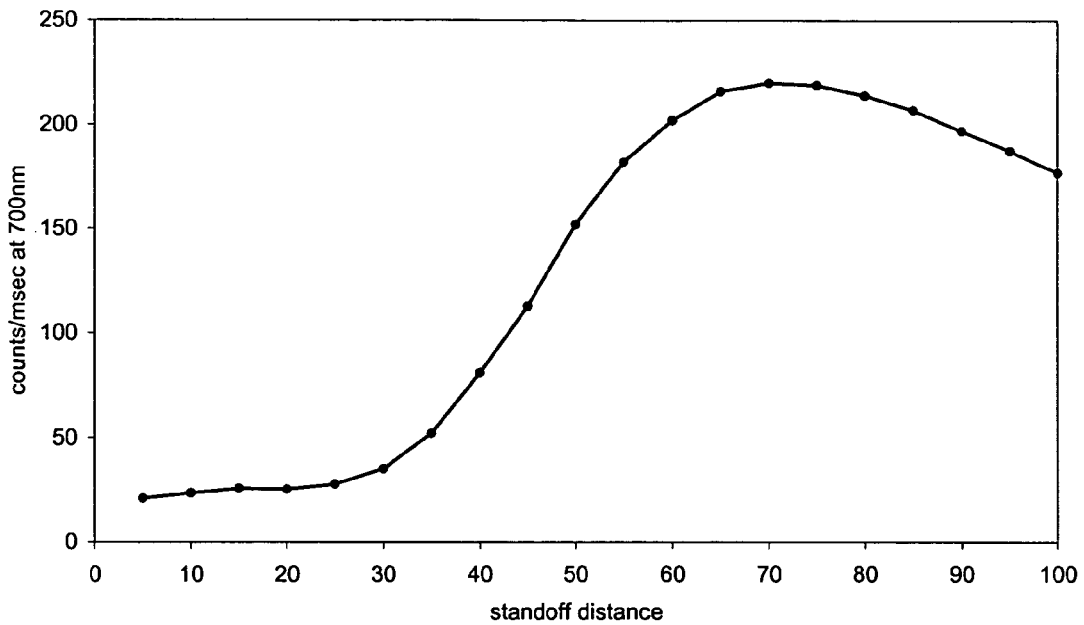
FIG. 5A is a graph showing the variation of reflectance intensity with stand-off distance for a source-detector distance of 30 mm.
Figure 5B:
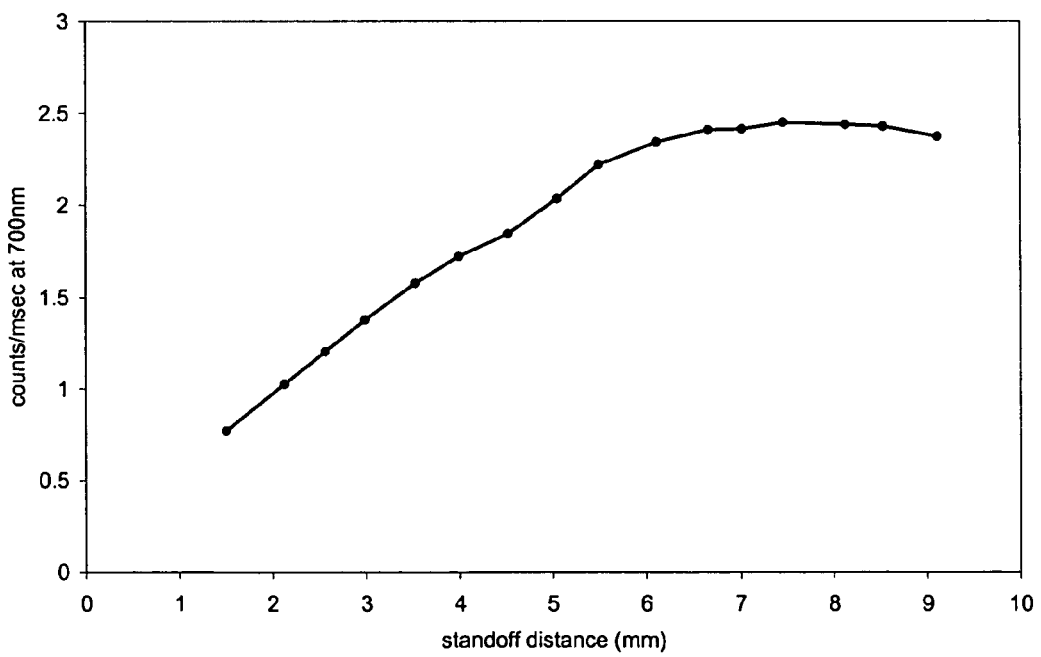
FIG. 5B is a graph showing the variation of reflectance intensity with stand-off distance for a source-detector distance of 2.5 mm.

As an example, FIG. 5A and FIG. 5B show measurements of diffuse reflectance counts (D) as a function of probe-to-target distance (PTD)—also referred to as stand-off distance—for two different probe configurations. FIG. 5A shows data recorded from a measurement system in which the distance between the source and detector (i.e., between fiber bundles 116a and 116b, respectively) is about 30 mm. The maximum D value, corresponding to an angle of incidence that matches the measured and nominal reflectances of target 402, appears at a PTD of about 70 mm. FIG. 5B shows data recorded from a measurement system in which the spacing between fiber bundles 116a and 116b is about 2.5 mm. The PTD that most closely matches the measured and nominal reflectances of target 402 in this configuration is about 7.5 mm.

Based on the chosen probe-to-target distances, reference stand-off blocks can be incorporated into measurement systems in order to facilitate reference measurements. Stand-off blocks may be particularly useful for instruments designed to be used in field applications where access to laboratory positioning equipment for determining the optimum PTD may not be available. FIG. 6A shows an example of a measurement system that includes fiber bundle 116 and reflectance target 402. Stand-off 502 is positioned between fiber bundle 116 and target 402 and ensures that a probe-to-target distance $d_1$ of about 70 mm is maintained between the two, and further ensures that the distance between fiber bundles 116a and 116b is about 30 mm.

In another configuration of a measurement system, FIG. 6B shows an example of a measurement system that includes fiber bundle 116, reflectance target 402, and stand-off 504 positioned between the fiber bundle and the target. Stand-off 504 ensures that a probe-to-target distance $d_2$ of about 7.5 mm is maintained, and further ensures that the distance between fiber bundles 116a and 116b is about 2.5 mm.

FIG. 7 shows in greater detail an example of a reflectance target 402 for use in a visible portion of the electromagnetic spectrum. The target shown includes a first reference block 402a having a standardized reflectance of 99%, a second reference block 402b having a standardized reflectance of 50%, and a third reference block 402c having a standardized reflectance of 2%. As discussed above, reflectance targets may be chosen to include three or more reference blocks with standardized reflectances that span a range of reflectances measured from one or more samples under measurement.

One or more targets 402 can be included, for example, in the housing of the spectroscopic system such that they are protected from damage, stray light, and changes, and located in a position in which a user can easily place the fiber optic probe 116b over the target to begin the standardization. The user could also place the probe 116b in a fixed location while the different targets 402 are consecutively moved into position proximate to the probe, such that their spectra can be measured. For example, different targets could be moved linearly past the fixed position of the probe, or the probe could be placed at a radial distance from the center of a circular target having multiple sections, each having a different reflectivity, and the target could be rotated to pass each section into optical communication with the probe. Movement of either the probe or the targets can be accomplished manually by a system operator. Alternatively, either (or both) of the probe and the targets can be mounted on a motorized stage or holder that provides for translation of the probe and/or targets, either in response to a control signal from a computer (such as computer 118) or in fully automated fashion.

Figure 15:
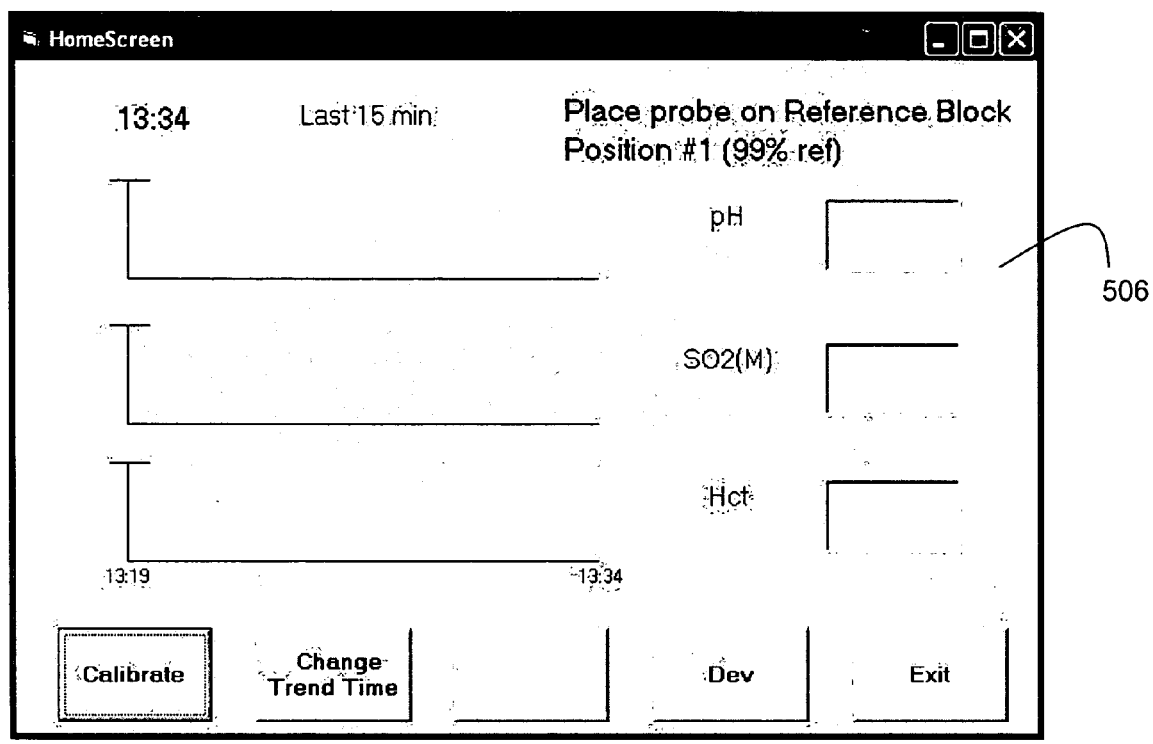
FIG. 15 is a computer screen capture showing a calibration and measurement computer program that can provide prompts to a system operator.

Many of the steps involved in measurement system standardization may be controlled or performed by computer 118, or by a system operator in response to prompts from the computer. As an example, during a standardization procedure, software running on computer 118 may prompt the operator to (or may automatically) perform reflectance measurements on the 99%, 50%, and 2% reflectance standards shown in FIG. 7 at each of the large and small separations (30 mm and 2.5 mm, respectively) between fiber bundles 116a and 116b. This yields a total of six separate reference reflectance measurements. The operator can choose an appropriate integration time for collecting the reflectance data, or computer 118 may contain software instructions and algorithms that automate the selection of the optimum integration time based on a maximum in a detected signal intensity. Computer 118 can also include a user interface, such as interface 506 shown in FIG. 15, associated with a computer program that performs calibration functions for a measurement system. The user interface can prompt a system operator to alternately configure the probe to collect reflectance data from each of the selected reflectance targets. For example, in FIG. 15, the user interface provides a prompt to an operator to "Place probe on Reference Block Position #1 (99% ref)". The interface can also prompt the operator to configure the system for one of the selected stand-off distances. Additional prompts and information, such as the elapsed time since re-calibration of the measurement system, and the calculated results of measurements of quantities of interest such as pH, muscle oxygen saturation ($SO_2$), and blood hematocrit (Hct), can also be displayed on the user interface.

In general, differences in measurement system throughput can be attributed to differences in the efficiency of individual optical components, and so the optimum integration time will vary from one measurement system to another. Consequently, in a subsequent step, a measured intensity spectrum can be normalized with respect to the integration time to produce a temporal intensity spectrum in units of intensity counts per unit time. Time may be measured in milliseconds, for example.

Calibration data recorded and calculated during the system standardization procedure can be stored in a selected location for each measurement system, from where the data can be accessed for real-time standardization of the system prior to or during use. For example, a user interface associated with a software program running on computer 118 can provide an option to re-calibrate the measurement system for each new subject or sample.

Spectra measured with a measurement system, $R_X^{meas}(\lambda)$, are compared with the standard reflectivity spectra, $R_X^{std}(\lambda)$, to calibrate the response of the system at each of the 2048 wavelength intervals. From the comparison of $R_X^{meas}(\lambda)$ and $R_X^{std}(\lambda)$ at each wavelength interval, a polynomial model fitting the measured reflectivity to the actual reflectivity is developed according to the equation, $$\tilde{R}(\lambda) = a_\lambda R^2(\lambda) + b_\lambda R + c_\lambda, \quad (4)$$

where $\tilde{R}(\lambda)$ is the scaled reflectance value, $R(\lambda)$ is the measured reflectance value, and a, b, and c are wavelength- and system-dependent polynomial coefficients for a particular wavelength interval. Thus, developing coefficients a, b, and c for every spectroscopic system 100 standardizes the scaled reflectivity spectra measured by every spectroscopic system to NIST-traceable standards. After calibration, actual reflectivity spectra measured on a real sample (e.g., tissue, blood, grain), $R^{meas}(\lambda)$, can be corrected for instrument-specific errors with Equation (4). Scaled reflectance spectra, $\tilde{R}(\lambda)$, measured by a system are subsequently converted into absorbance units using the basic Beer's law for light attenuation, $$\tilde{A} = \text{Log}_{10}\left(\frac{1}{\tilde{R}}\right), \quad (5)$$

where $\tilde{A}$ is the absorbance spectrum calculated from the scaled reflectance measurements.

Equation (4) is used to model the scaled reflectance as a second-order function of the measured reflectance $R(\lambda)$. In general, however, other functional forms may be used in place of quadratic Equation (4). In particular, the scaled reflectance can be expressed as a higher-order polynomial (e.g., third-order, fourth-order, fifth-order or higher) in the measured reflectance, or in terms of another functional form that includes one or more fitting parameters, in which the scaled reflectance is a dependent variable and the measured reflectance is an independent variable.

Correction for Additional Effects

Although the above calibration technique can be used to standardize the response of multiple systems to well-characterized reflectors (e.g., NIST-traceable reference standards), non-linear and other effects within a sample (e.g., light scattering within the sample) can cause the reflectivity spectra measured by spectroscopic systems having different collection efficiency and/or different lamp outputs to be vertically offset from each other in an $\tilde{A}$ vs. $\lambda$ graph. Samples exhibiting such non-linear effects can include tissue and blood samples.

In some measurement systems, the errors introduced by these effects are not large enough to warrant further correction of the measured reflectance or absorbance data. However, in other systems, these effects—and the vertical offsets they introduce—are compensated using one or more additional techniques.

For example, a first method of correcting for scattering and other processes in tissues includes fitting a modified Beer's Law equation to the scaled absorbance data obtained from Equation (4) to derive estimates of quantities of interest such as tissue oxygenation. Examples of a modified Beer's Law equation are disclosed, for example, in Nighswander-Rempel et al., "Mapping tissue oxygenation in the beating heart with near-infrared spectroscopic imaging," Vibr. Spectr. 32: 85-94 (2003), the contents of which are incorporated herein by reference in their entirety. The fitting algorithm can compensate for variations in the near-IR reflectance spectrum that arise due to variations in optical path length and tissue scattering in non-homogeneous subjects. This method essentially provides a scaling adjustment of the absorbance data.

A second method of correcting for scattering and other processes (e.g., non-linear effects) in absorbance data includes performing an additional scaling step on the scaled absorbance spectra, $\tilde{A}(\lambda)$, by means of a standard normal variate ("SNV") transformation technique as described, for example, in Barnes et al., "Standard normal variate transformation and detrending of near-infrared diffuse reflectance spectra," Appl. Spectrosc., 43:772-777, (1989), the contents of which are incorporated herein by reference in their entirety. As a result of performing the SNV transformation, the transformed absorbance spectra have a zero mean value and a standard deviation equal to one. In particular, the spectral matrix, $\tilde{A}(\lambda)$, is converted by a SNV transformation to $\tilde{A}^{snv}(\lambda)$ with the equation, $$\tilde{A}^{snv} = \frac{(\tilde{A} - \mu)}{\sqrt{\dfrac{\sum_{j=1}^{p}(\tilde{A}_j - \mu)^2}{p-1}}}, \quad (6)$$

where $\tilde{A}^{snv}$ is the SNV corrected absorbance spectrum of the sample, $\tilde{A}$ is the absorbance spectrum of the sample that is calculated from its scaled reflectance spectrum, $\tilde{R}$, using Equation (5), $\mu$ is the average of $\tilde{A}$ across p wavelengths for the sample, and j is an index of the wavelength interval in the absorbance spectrum. Because SNV normalization requires that $\tilde{A}^{snv}$ be mean-centered, $\tilde{A}^{snv}$ may have negative values. The standardized and SNV-normalized spectrum, therefore, is rescaled such that the minimum absorbance value is positively offset from zero. After standardization and SNV normalization, the spectra reported from two different spectroscopic systems are very similar.

In addition to standardizing a spectroscopic system initially, the user can be alerted at regular intervals to re-standardize the system or automatically when the standardization procedure needs to be reapplied to correct for any degradation of the optical components of the system over time. For example, every time the instrument is used, the spectrum of a reference standard (e.g., a 99% or 50% reflectance standard) can be measured and compared to a spectrum that was measured on the same standard when the system was initially standardized. The initial spectrum of the reference standard for the instrument can be stored in the computer 118 when the instrument is first assembled and standardized. Then, every time the instrument is turned on, the spectrum of the reference standard is measured again and compared with the stored spectrum. When the comparison shows a deviation between the two spectra by a predetermined amount (e.g., indicating reduced light output, broken fibers, and/or degraded detector performance) an error message is provided to the user suggesting that the unit be re-standardized so that new a, b, and c coefficients in Equation (4) can be calculated.

Implementation

The equations and algorithms described herein can be easily implemented in hardware or software, or a combination of both. The invention can be implemented in computer programs using standard programming techniques following the method steps, equations, and figures disclosed herein. The programs should be designed to execute on programmable processors or computers, e.g., microcomputers, each including at least one processor, at least one data storage system (including volatile and non-volatile memory and/or storage elements), at least one input device, such as a keyboard or push button array, and at least one output device, such as a CRT, LCD, or printer. Program code is applied to input data to perform the functions described herein. The output information is applied to one or more output devices such as a printer, or a CRT or other monitor, or a web page on a computer monitor with access to a website, e.g., for remote monitoring.

Each program used in the new system is preferably implemented in a high level procedural or object oriented programming language to communicate with a computer system. However, the programs can be implemented in assembly or machine language, if desired. In any case, the language can be a compiled or interpreted language.

Each such computer program is preferably stored on a storage medium or device (e.g., ROM, CD, magnetic diskette, hard drive, or other computer memory) readable by a general or special purpose programmable computer (e.g., a "computer-readable medium" or a "machine-readable medium"), for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein. In addition, software embodying the new methods can be transmitted via a wired or wireless communications network, such as an intranet, or the Internet. The software can be downloaded directly into a memory of a sensor unit, or onto a machine-readable medium.

Uses of the Methods and Systems

Following calibration of a measurement system, a mathematical model relating a measurement of a spectrum of a sample to a property of interest can be generated and applied to, or replicated and introduced or loaded into, other calibrated measurement systems. For example, a first measurement system can be calibrated using any of the previously described methods. Then, the spectrum of a reference specimen having a known value of a property of interest (e.g., pH, $SO_2$, hemoglobin content, and others) can be measured using the first measurement system. A mathematical model, such as a modified Beer's law equation (as discussed above), can be used to quantify the relationship between the measured spectrum and the known value of the property of interest. Numerical techniques such as regression analysis can be used to calculate values of adjustable parameters in the mathematical model. Spectral measurements on other samples can then be used, together with the mathematical model and the calculated model parameters, to determine values of the property of interest for the other samples. In general, a wide variety of models correlating the measured spectrum of a sample to its properties can be employed. For example, models correlating the pH of a sample to a measured sample spectrum are disclosed in U.S. Pat. No. 5,813,403 entitled "OPTICAL MEASUREMENT OF TISSUE PH" by Babs R. Soller et al., filed on Nov. 8, 1995, the entire contents of which are incorporated herein by reference. Models correlating hematocrit measurements of a sample to the sample's spectrum are disclosed, for example, in U.S. Pat. No. 6,006,119 entitled "NON-INVASIVE OPTICAL MEASUREMENT OF BLOOD HEMATOCRIT" by Babs R. Soller et al., filed on Feb. 4, 1998, the entire contents of which are incorporated herein by reference.

Further, models generated on the first measurement system can be applied to, or replicated and loaded into (e.g., hard wired or by use of software), other measurement systems. For example, a second measurement system can also be standardized using any of the disclosed methods. Thereafter, mathematical models and their associated parameters that are determined on the first measurement system can be replicated to the second measurement system (and any other measurement systems that have been similarly calibrated) without requiring further correction or adjustment. Thus, very accurate models relating the measured spectrum of a sample to a property can be implemented in many measurement systems without the need for additional calibration steps. Essentially, standardization of the measurement systems can remove a dependence of measured spectra on small variations in the position, configuration, and performance of various components in each of the measurement systems.

Replicating a model in a measurement system can be accomplished in many ways. For example, the model may be stored on a storage medium such as a computer readable storage medium (e.g., computer memory, magnetic or optical storage medium, a computer-readable file located at a network address such as an Internet address). Alternatively, the model may be replicated by a copying operation from one machine to another, or via manual entry of the model by an operator.

The new standardization methods can be used in any field where diffuse reflectance spectroscopy is performed, including, for example, noninvasive medical measurements, chemical and pharmaceutical plant process control, and environmental monitoring. Samples that can be examined using the measurement systems described herein include human tissues and human-derived fluids such as blood, urine, and saliva. Tissue and blood samples from other plant and animal specimens are also amenable to study. Agricultural products (e.g., melons), natural products (e.g., soil, forestry products), and petroleum (and petroleum-derived substances) can also be examined. Measurements can generally be performed on both in vitro and in vivo samples.

For example, quantities which can be determined from standardized reflectance measurements include, but are not limited to, pH (e.g., muscle pH), oxygen pressure $PO_2$ (e.g., muscle $PO_2$), oxygen saturation and/or content of blood or tissue ($SO_2$), hemoglobin concentration, blood hematocrit, concentrations of lactate and glucose, and concentrations of ions such as sodium, potassium, and calcium. Further, measures of tissue perfusion in a living patient can be simultaneously and non-invasively determined using near-IR spectroscopy. The spectroscopic system can also be used to monitor data other than information concerning living patients, such as concentrations of air-born, water-born, and solid-born chemicals.

It should be noted that while stand-offs are typically used when standardizing a selected measurement system against a known reflectance target, stand-offs or other similar devices are generally not required when making reflectance measurements from subjects (i.e., patients and/or tissue samples) because a subject typically reflects light over a distribution of angles, and at least a portion of the reflected light will be at a suitable angle for coupling into the probe in most cases. Therefore, the probe-to-sample distance when measuring reflectance from a subject is, in many cases, essentially a free parameter. Thus, placement of the probe relative to the sample surface may be chosen for reasons of measurement convenience. As long as the amount of reflected light collected by the probe fiber bundle is sufficient to yield a signal on a detector, the probe placement can be varied as desired.

EXAMPLES

The invention is further described in the following examples, which do not limit the scope of the invention described in the claims.

Example 1

Testing of Tissue Phantoms

Tissue-mimicking phantoms were used to validate to the spectral standardization method. The phantom scattering properties were provided by 20% INTRALIPID® (available from Fresenius Kabi Clayton LP, Clayton, N.C.), an emulsion of phospholipid micelles and water. Due to the negligible absorption properties of intralipid in the visible and near infrared, the attenuation of light by the intralipid fat micelles is assumed to be wholly due to scattering. The scattering properties (quantified as the scattering coefficient) of the intralipid was determined by the method described by van Staveren et al., Appl. Opt., 30:4507-4514 (1991), the entire contents of which are incorporated herein by reference.

The phantom absorbing properties were provided with lyophilized human hemoglobin (Part# H7379-10G, available from Sigma-Aldrich Inc., St Louis, Mo.). The form of hemoglobin present in lyophilized hemoglobin powder is methemoglobin (i.e., the ferric or $Fe^{3+}$ derivative of hemoglobin). Methemoglobin (metHb) has a prominent absorption peak at 632 nm, as described by Zijlstra et al., Clin. Chem., 37:1633-1638 (1991), the entire contents of which are incorporated herein by reference. MetHb was used in lieu of blood because unlike the hemoglobin in blood (primarily oxyhemoglobin), metHb is stable, thereby ensuring control over the phantom's absorption properties over a fairly lengthy period. The metHb concentration was independently determined with a colorimetric cyanmethemoglobin method, in which metHb is converted to the cyano-derivative and measured at 540 nm, as described in Drabkin and Austin, J. Biol. Chem., 112:51-65 (1935), the entire contents of which are incorporated herein by reference. The conversion of metHb solution to the cyano-derivative was accomplished with Drabkin's reagent™ (Part# D5942, available from Sigma-Aldrich Inc.), which amongst other things, contains the cyanide salt used for this transformation.

The phantoms were created with agar (Part# A7049-500G, available from Sigma-Aldrich Inc.), 50 ml of water, intralipid, and metHb. To fabricate a phantom an initial mixture of agar and water was facilitated by the application of heat. Intralipid and metHb were added to the agar matrix after cooling to 60° C. and 42° C. respectively. The resulting mixture was mixed thoroughly until the uniformity of the overall solution was visually confirmed. The proportion of intralipid in each phantom was 7.5% (v/v), which corresponds to a reduced scattering coefficient of 1.5 mm to 1 at 760 nm. The reduced scattering coefficient of the phantoms is consistent with the experimentally determined value for human tissue, as described in Doornbos et al., Phys. Med. Biol., 44:967-981 (1999), the entire contents of which are incorporated herein by reference. Fifty phantoms were made in which the metHb concentration varied from 3 to 18 g/dl. The phantoms were cast into plastic Petri dishes that were ½ inch deep and 2 inches in diameter. After solidifying, each phantom was extracted from its respective mold, wrapped in cellophane, and refrigerated. The optical properties of each phantom layer were maintained for up to 48 hours.

Figure 8:
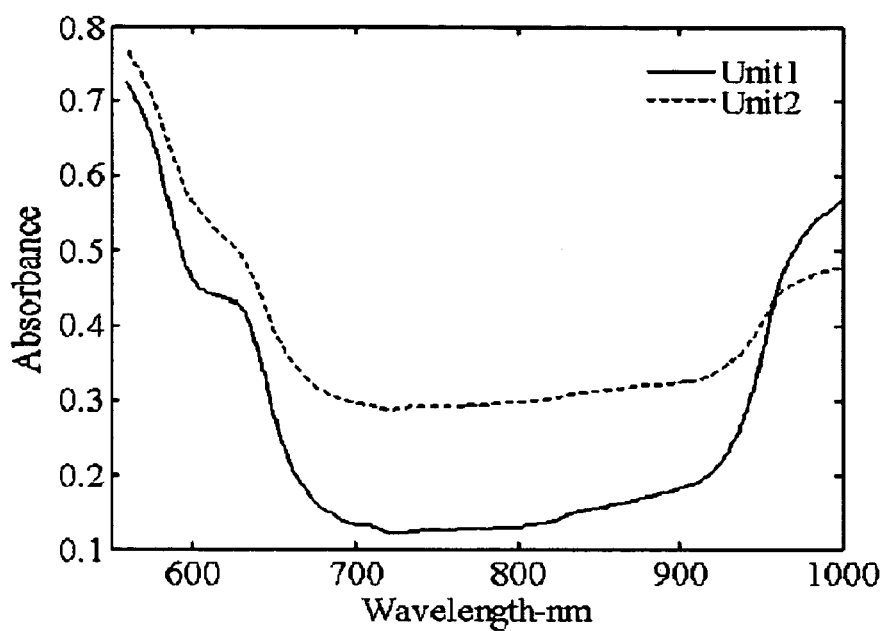
FIG. 8 is a comparison of sample spectra measured by two different spectroscopic units.
Figure 9:
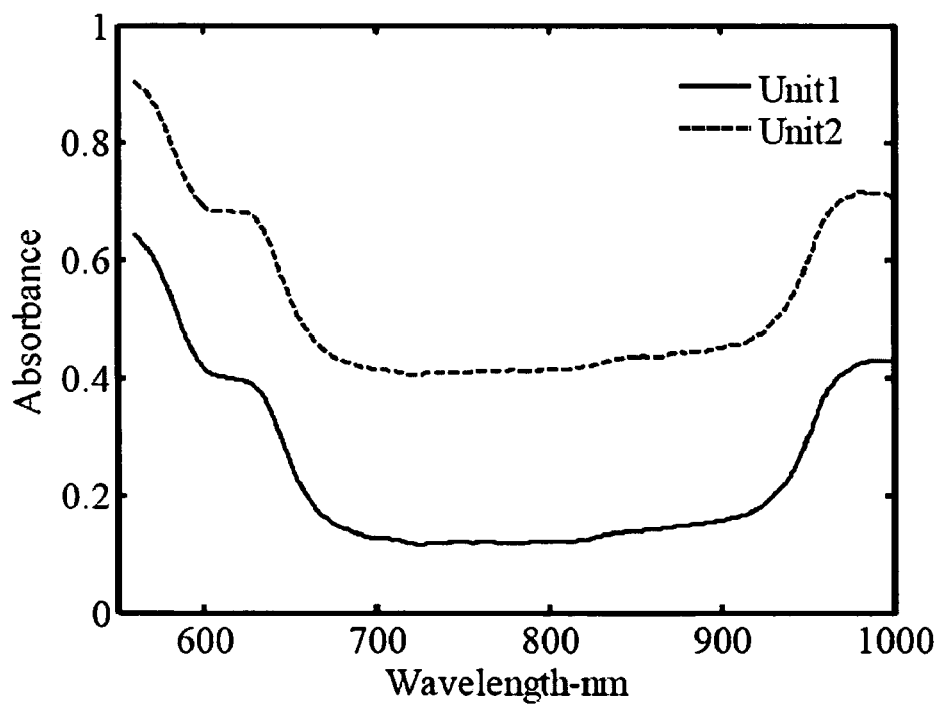
FIG. 9 is a comparison of sample spectra measured by two different spectroscopic units that have been standardized with a traceable physical standard.
Figure 10:
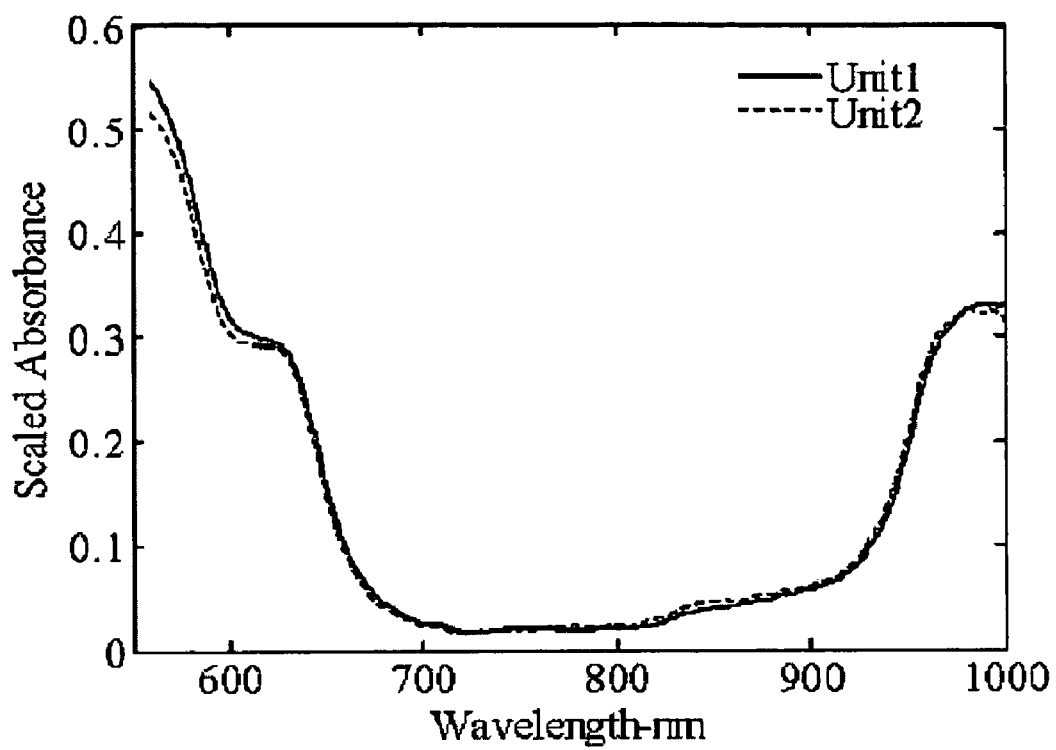
FIG. 10 is a comparison of spectra of a sample measured by two different spectroscopic units that have been standardized with a traceable physical standard after the spectra have been normalized with a standard normal variate algorithm.

Spectra of the 50 phantoms were measured by two different, nominally-identical spectroscopic units that had not been standardized. Three spectra were obtained for each phantom by each unit by placing the fiber optic probe 116a at different spatial locations on the phantom, and the three spectra were averaged. The average spectra of the 50 targets measured with two different, nominally-identical systems (designated as unit 1 and unit 2) shown in FIG. 8, clearly show that without standardization two quite different spectra can result. Although spectroscopic features of the phantom are evident in the spectra measured by both systems, the two spectra are skewed and offset from each other. After standardization of the two units, the spectra of the 50 phantoms were measured and averaged again. These spectra, shown in FIG. 9, show good agreement except for a vertical offset between the spectra measured by the different systems, which could be due to different lamp outputs or collection efficiencies between the two systems. After processing the averaged spectra shown in FIG. 9 with the SNV normalization of Equation (6), the spectra measured by the two different systems are very similar, as shown in FIG. 10.

Figure 11A:
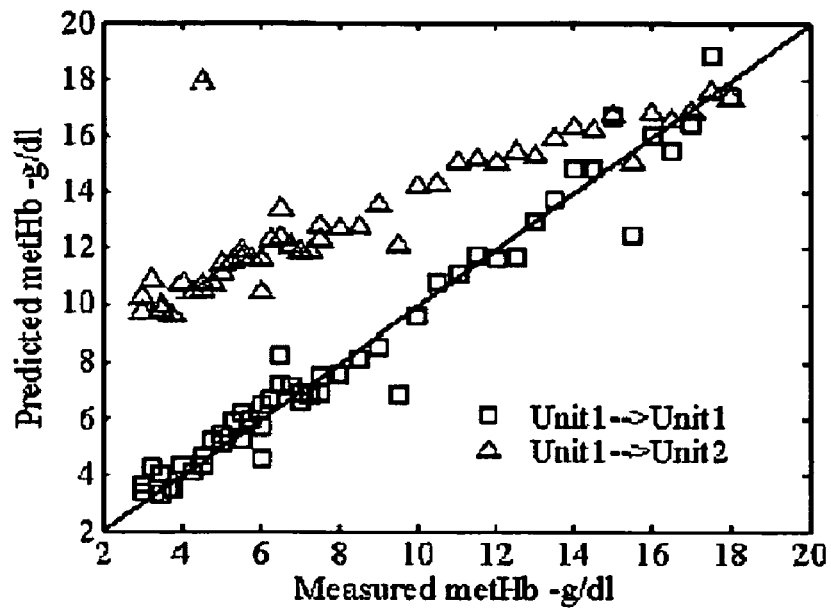
FIG. 11A is a comparison of metHb concentration values of different samples calculated from uncorrected spectra recorded with two different units with actual metHb concentration values for the samples.
Figure 11B:
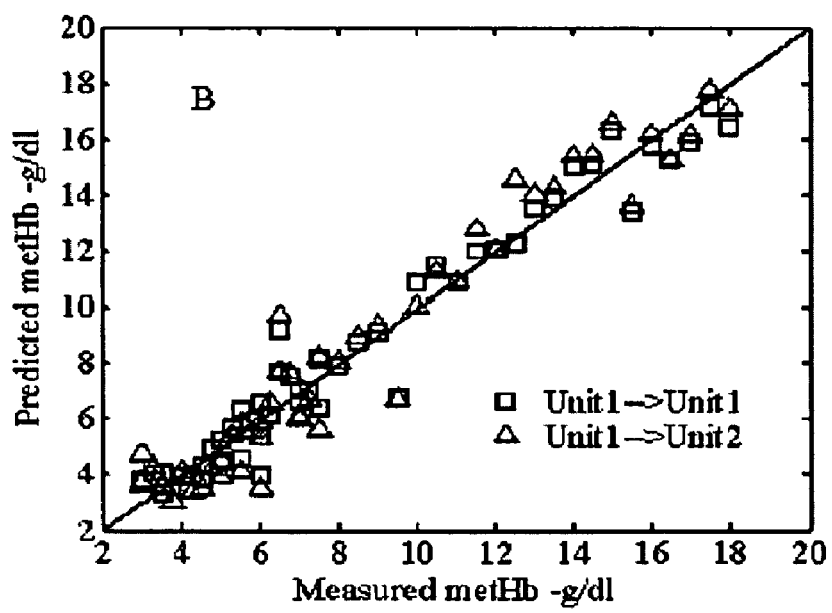
FIG. 11B is a comparison of metHb concentration values of different samples calculated from SNV normalized spectra recorded with two different standardized units with actual metHb concentration values for the samples.

A PLS model for determining the amount of metHb in a sample was developed based on the spectra taken with one unit of the 50 phantoms and the known hemoglobin concentration in the 50 phantoms. Using the calculated PLS model for metHb that was developed on the first unit, the metHb concentration was estimated from phantom spectra that were acquired by units 1 and 2. FIG. 11A compares the metHb values calculated from uncorrected spectra recorded with unit 1 (open squares) and unit 2 (open triangles) for the 50 phantoms with the actual metHb values for the 50 phantoms. FIG. 11B compares the metHb values calculated from the spectra recorded with unit 1 (open squares) and unit 2 (open triangles) for the 50 phantoms with the actual metHb values for the 50 phantoms after the units have been standardized and the spectra have been processed with the SNV algorithm.

As can been seen from a comparison of FIGS. 11A and 11B, the success of replicating a PLS model developed on one unit to another unit depends on standardizing the units. A model fit error, $RMSE_{unit1 \to unit1}$, can be determined by comparing the reference metHb concentration in the 50 phantoms, to those estimated metHb concentrations obtained by comparing the measured spectra to the model according to the following equation, $$RMSE = \sqrt{\sum_{i=1}^{N} \frac{(y_i - \hat{y}_i)^2}{N}}, \quad (7)$$

where N is the number of phantoms (i.e., 50), $\hat{y}_i$ is the estimated metHb concentration for the $i^{th}$ sample, and $y_i$ is the actual metHb concentration for the $i^{th}$ sample. The model calculated from samples measured with unit 1 was applied to the standardized and non-standardized absorbance spectra of same samples on unit 2 ($\tilde{A}_{unit2}$, $A_{unit2}$). The model fit error in unit 1 ($RMSE_{unit1 \to unit1}$) was calculated as 0.85 g/dl, and the model fit error of the metHb concentration values calculated from unstandardized spectra collected with unit 2 was calculated to be 4.94 g/dl.

As shown in FIG. 11B, spectral standardization results in a better replication of the PLS model from unit 1 to unit 2. In particular, the $RMSE_{unit1 \to unit2}$ is improved to 1.15 g/dl when the units are standardized and the spectra are normalized using a SNV technique. When spectra are normalized, there is a slight degradation in the baseline model performance on unit 1, and $RMSE_{unit1 \to unit1}$ increases to 0.94 g/dl. This increase may be caused because the SNV transformation adjusts the baseline levels in the spectra and therefore removing portions of the analyte (metHb) information that is correlated to the baseline shifts. However, the degradation in model performance is very small.

Example 2

Testing of Volunteer Subjects During Emergency Medical Care

Figure 12A:
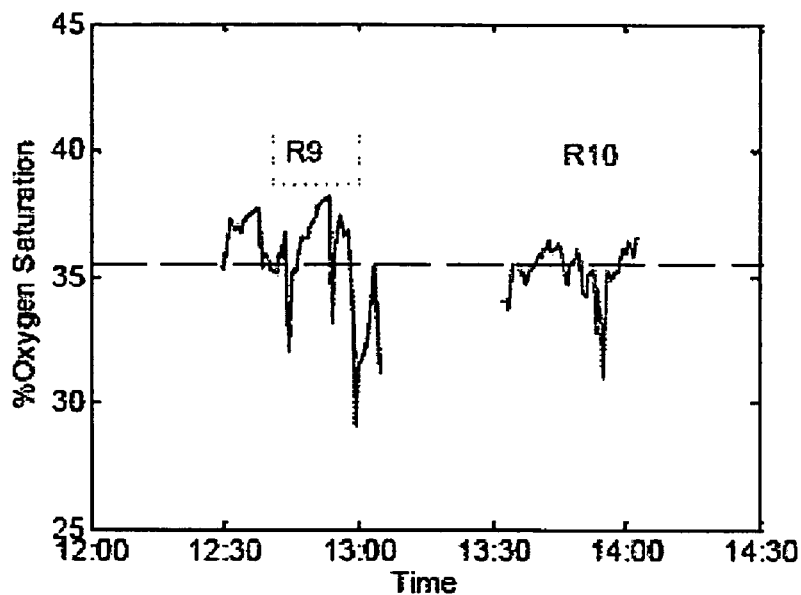
FIG. 12A is a graph showing percent oxygen saturation as a function of time for two different, independently-standardized measurement systems.

The standardization methods described herein were further evaluated using data collected from a volunteer subject undergoing emergency medical treatment. Near-IR spectra were collected using two different measurement systems, each standardized against a series of reflectance targets. The measured reflectances were used to derive scaled reflectance and absorbance values according to Equations (4) and (5), but a separate SNV step was not used to rescale the absorbance values. Instead, a modified Beer's law equation was used to further correct the absorbance data for light scattering by tissue and other effects. FIG. 12A shows results for 30 minutes of muscle oxygen saturation measurements ($SO_2$) from two different, standardized measurement systems R9 and R10. Variations in the measurements of tissue $SO_2$ over the measurement period reflect changes in tissue physiology. However, the mean values of $SO_2$ for each measurement set are statistically equivalent (35.3% for R9 and 35.7% for R10), which confirms the accuracy of the standardization methods disclosed herein.

Figure 12B:
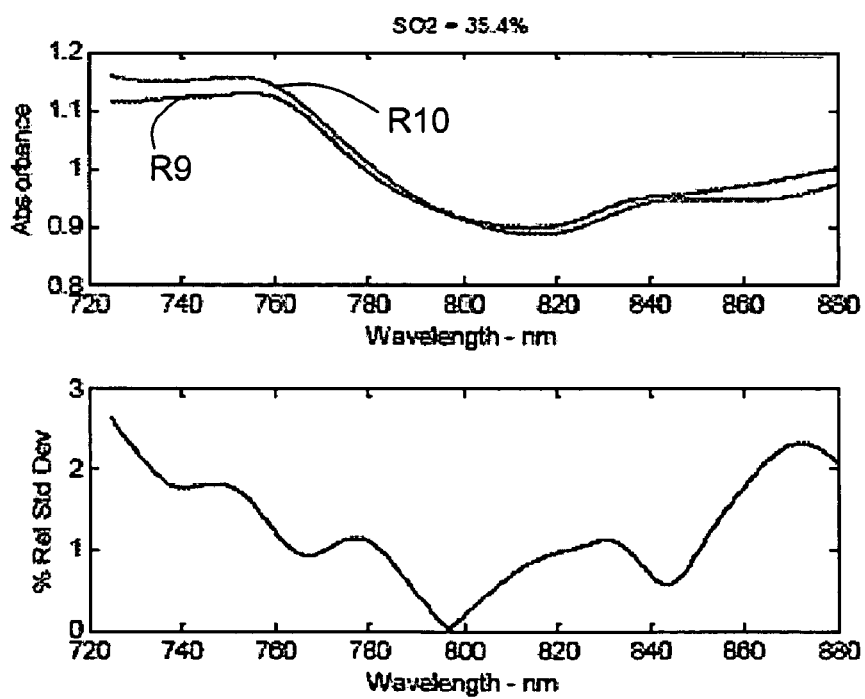
FIG. 12B is a graph showing near-IR absorbance measurements and their standard deviations for two different, independently-standardized measurement systems.

FIG. 12B (upper panel) shows a comparison between the near-IR absorbance spectra calculated from the data measured by the R9 and R10 systems. Each spectrum corresponds to an estimated $SO_2$ value of about 35.4%. The lower panel of FIG. 12B shows the relative standard deviation between the absorbance spectra derived from R9 and R10. The relative standard deviation is less than 3% for all wavelengths in the spectral region from 720 nm to 880 nm, and the mean relative standard deviation is about 1.3%.

Example 3

Testing of Volunteer Subjects During Periods of Exercise

The disclosed standardization methods were further tested by making measurements of muscle oxygen saturation $SO_2$ from two different volunteer subjects using different measurement systems that were standardized prior to recording data from the subjects. The subjects undertook periods of exercise, the intensity of which was expressed in terms of a mean voluntary contraction (MVC). Near-IR reflectance measurements from each of the subjects were mathematically processed to produce scaled reflectance and absorbance values according to Equations (4) and (5). The scaled absorbance data were subsequently used as input to a modified Beer's law equation to calculate estimates for $SO_2$ in each of the subjects.

FIGS. 13A and 13B show calculated $SO_2$ for a first subject under varying levels of exercise-induced stress. FIG. 13A shows measurements at MVC levels of 30% and 40% taken with a first measurement system (denoted RM2C23) which was standardized using a reflectance target denoted "Avian 3". The measurements were recorded over a period of about 90 minutes. FIG. 13B shows measurements from the same subject at MVC levels of 50% and 40% taken with a second measurement system (denoted RM5C20), that was standardized against a different reflectance target ("Avian 1"). The measurements of $SO_2$ shown in FIG. 13B were recorded over a period of about 90 minutes, and after the measurements shown in FIG. 13A. The $SO_2$ values at the end of the first measurement sequence (FIG. 13A) and at the beginning of the second measurement sequence (FIG. 13B) are closely matched, indicating the success of the standardization procedure used for the first and second measurement systems.

FIGS. 14A and 14B show calculated $SO_2$ data for a second subject under similar conditions of exercise-induced stress. In FIG. 14A, a third measurement system (RM4C22) was standardized against a reflectance target "Avian 6", and the calculated $SO_2$ values, derived from measurements taken over a period of about 65 minutes, are shown. In FIG. 14B, a fourth measurement system RM5C20 was standardized against a reflectance target "Avian 1" and used to make near-IR tissue reflectance measurements over a period of about 90 minutes from the same subject following the sequence of measurements shown in FIG. 14A. Estimates of $SO_2$ were derived as in the other measurement scenarios. The close matching of the $SO_2$ values at the end of the first measurement sequence (FIG. 14A) and at the beginning of the second measurement sequence (FIG. 14B) indicates the success of the standardization procedure used for the third and fourth measurement systems.

OTHER EMBODIMENTS

It is to be understood that while implementations been described in conjunction with the detailed description thereof, the foregoing description is intended to illustrate and not limit the scope of the invention that can be claimed.

What is claimed is:

1. A method of determining a value of a property of a sample with a spectroscopic system, the method comprising:
    measuring, with a first spectroscopic system, spectra of a first set of at least three different reference targets, each having a known, unique reflectivity spectrum;
    calibrating the first spectroscopic system based on the spectra of the first set of reference targets measured by the first spectroscopic system;
    measuring, with the first spectroscopic system, a spectrum of a known reference specimen having a known value of a property;
    generating a model for determining the property on the first spectroscopic system using the spectrum of the known reference specimen;
    measuring, with a second spectroscopic system, spectra of a second set of at least three different reference targets, each having a known, unique reflectivity spectrum;
    calibrating the second spectroscopic system based on the spectra of the second set of reference targets measured by the second spectroscopic system;
    applying the model to the second spectroscopic system;
    measuring a spectrum of a sample using the second spectroscopic system; and
    determining a value of the property of the sample based on the spectrum of the sample measured by the second spectroscopic system using the model.

2. The method of claim 1, wherein calibrating the first spectroscopic system comprises calculating a set of calibration coefficients $a_1$, $b_1$, and $c_1$.

3. The method of claim 1, wherein calibrating the second spectroscopic system comprises calculating a set of calibration coefficients $a_2$, $b_2$, and $c_2$.

4. The method of claim 1, wherein the three different unique reflectivity spectra for the first set of targets are the same as the three different unique reflectivity spectra for the second set of targets.

5. The method of claim 1, wherein at least one of the three different unique reflectivity spectra for the first set of targets is different than one of the three different unique reflectivity spectra for the second set of targets.

6. The method of claim 1, wherein the first and second spectroscopic systems are calibrated using a wavelength standard prior to measuring the spectra of the reference targets.

7. The method of claim 6, wherein the wavelength standard is a mercury-argon lamp.

8. The method of claim 1, wherein the reflectivity spectra of the reference targets are traceable to a standard.

9. The method of claim 1, further comprising determining an optimum stand-off distance between a probe of the first and second spectroscopic systems and a reference target.

10. The method of claim 9, wherein determining an optimum stand-off distance comprises measuring a reflectance intensity as a function of a distance between the probe and the reference target, and selecting the distance at which the reflectance intensity is highest.

11. The method of claim 1, wherein the spectrum of the sample measured using the second spectroscopic system is corrected prior to determining a value of the property.

12. The method of claim 11, wherein the correction comprises normalizing the spectrum with a standard normal variate algorithm.

13. The method of claim 1, wherein the value of the property is determined using a modified Beer's law equation.

14. The method of claim 1, wherein the sample comprises human tissue.

15. The method of claim 1, wherein the sample is selected from the group consisting of blood, urine, and saliva.

16. The method of claim 1, wherein the sample is selected from the group consisting of tissue, blood, agricultural products, pharmaceuticals, natural products, and petroleum.

17. The method of claim 1, wherein the sample is an in vitro sample.

18. The method of claim 1, wherein the sample is an in vivo sample.

19. The method of claim 1, wherein the property is an amount of hemoglobin in the sample.

20. The method of claim 1, wherein the property is oxygen saturation, content, or pressure in the sample.

21. The method of claim 1, wherein the property is a pH of the sample.

22. The method of claim 1, wherein the property is a concentration of lactate or glucose in the sample.

23. The method of claim 1, wherein the property is a concentration of sodium ions, potassium ions, or calcium ions in the sample.

24. The method of claim 1, wherein the reflectivities of the at least three different reference targets measured with the first spectroscopic system span a range from about 2% to about 99%.

25. The method of claim 1, wherein the reflectivities of the at least three different reference targets measured with the second spectroscopic system span a range from about 2% to about 99%.

26. The method of claim 1, wherein the reflectivities of the at least three different reference targets measured with the first spectroscopic system are about 2%, about 50%, and about 99%.

27. The method of claim 1, wherein the reflectivities of the at least three different reference targets measured with the second spectroscopic system are about 2%, about 50%, and about 99%.

28. A standardized spectroscopic system comprising:
 a light source;
 a spectrograph;
 a probe for receiving light from the light source that is reflected by a target;
 a processor configured to:
  (a) direct the light source to shine incident light on at least three different reference targets:
  (b) direct the spectrograph to obtain reflectivity spectra of the at least three different targets by measuring incident light that is reflected by the targets and received by the probe;
  (c) calculate calibration constants from the reflectivity spectra; and
  (d) prompt an operator to re-standardize the spectroscopic system after a selected time interval has elapsed since a previous standardization sequence; and
 a memory for storing the calibration constants.

29. The system of claim 28, wherein the processor comprises computer program code having instructions that direct the processor to carry out the calculation of the calibration constants.

30. The system of claim 28, wherein the probe is a fiber optic probe.

31. The system of claim 28, further comprising at least one stand-off for maintaining the probe at a selected distance from the target.

32. The system of claim 28, wherein the processor is further configured to correct spectra obtained with the system using a standard normal variate algorithm.

33. The system of claim 28, wherein the processor is further configured to determine a value of a property of a sample by fitting a measured spectrum of the sample to a modified Beer's law equation.

34. The system of claim 28, further comprising a translation stage coupled to a driver for transporting the at least three different reference targets past a fixed position of the probe.

35. The system of claim 28, further comprising a translation stage coupled to a driver for transporting the probe past a fixed position of the at least three different reference targets.

36. The system of claim 28, further comprising the at least three different reference targets.

37. The system of claim 28, wherein the processor is further configured to provide prompts to an operator performing a series of steps comprising a standardization sequence.

38. The system of claim 28, wherein the processor is further configured to automatically perform a series of steps comprising a standardization sequence without operator intervention.

39. A spectroscopic system, comprising:
 a light source;
 a spectrograph;
 a probe for receiving light from the light source that is reflected by a target; and
 a processor configured to:

(a) receive information comprising a model for determining a value of a property using a different spectroscopic system, wherein the model is determined by:
  (i) measuring, with the different spectroscopic system, spectra of a first set of at least three different reference targets each having a known, unique reflectivity spectrum;
  (ii) calibrating the different spectroscopic system based on the spectra of the first set of reference targets;
  (iii) measuring, with the different spectroscopic system, a spectrum of a known reference specimen having a known value of the property; and
  (iv) generating the model for determining the value of the property using the different spectroscopic system from the spectrum of the known reference specimen;
(b) measure spectra of a second set of at least three different reference targets each having a known, unique reflectivity spectrum;
(c) calibrate the spectroscopic system based on the spectra of the second set of reference targets;
(d) apply the model to the spectroscopic system;
(e) measure a spectrum of a sample using the spectroscopic system; and
(f) determine a value of the property in the sample based on the spectrum of the sample using the model.

40. The system of claim 39, further comprising at least one stand-off for maintaining the probe at a selected distance from the reference targets.

41. The system of claim 39, wherein the processor is further configured to correct spectra measured using the system using a standard normal variate algorithm.

42. The system of claim 39, wherein the processor is further configured to determine the value of the property in the sample by fitting the measured spectrum of the sample to a modified Beer's law equation.

43. The system of claim 39, further comprising the second set of the at least three different reference targets.

* * * * *

UNITED STATES PATENT AND TRADEMARK OFFICE
CERTIFICATE OF CORRECTION

| | |
|---|---|
| PATENT NO. | : 7,881,892 B2 |
| APPLICATION NO. | : 11/337912 |
| DATED | : February 1, 2011 |
| INVENTOR(S) | : Soyemi et al. |

It is certified that error appears in the above-identified patent and that said Letters Patent is hereby corrected as shown below:

In Claim 28, col. 22, line 17, delete "targets:" and insert -- targets; --

Signed and Sealed this
Twenty-fourth Day of May, 2011

David J. Kappos
*Director of the United States Patent and Trademark Office*

UNITED STATES PATENT AND TRADEMARK OFFICE
CERTIFICATE OF CORRECTION

PATENT NO. : 7,881,892 B2
APPLICATION NO. : 11/337912
DATED : February 1, 2011
INVENTOR(S) : Olusola O. Soyemi Page 1 of 1

It is certified that error appears in the above-identified patent and that said Letters Patent is hereby corrected as shown below:

In the Specifications

Column 1, Line 19, under Statement as to Federally Sponsored Research, delete "may have" and insert --has--.

Signed and Sealed this
Twenty-first Day of May, 2013

Teresa Stanek Rea
*Acting Director of the United States Patent and Trademark Office*